US011059842B2

(12) United States Patent
D'Antonio

(10) Patent No.: US 11,059,842 B2
(45) Date of Patent: Jul. 13, 2021

(54) MONOSACCHARIDE AMINE AND 3-NITRO-2-PHENYL-2H-CHROMENE BASED INHIBITORS OF GLUCOSE KINASES

(71) Applicant: UNIVERSITY OF SOUTH CAROLINA, Columbia, SC (US)

(72) Inventor: Edward D'Antonio, Bluffton, SC (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 16/859,007

(22) Filed: Apr. 27, 2020

(65) Prior Publication Data

US 2020/0339619 A1 Oct. 29, 2020

Related U.S. Application Data

(60) Provisional application No. 62/840,005, filed on Apr. 29, 2019.

(51) Int. Cl.

| | |
|---|---|
| ***A61K 31/7048*** | (2006.01) |
| ***A61K 31/7008*** | (2006.01) |
| ***A61K 31/353*** | (2006.01) |
| ***A61P 33/02*** | (2006.01) |
| ***C07H 5/06*** | (2006.01) |

(52) U.S. Cl.

CPC ........... *C07H 5/06* (2013.01); *A61K 31/7008* (2013.01); *A61K 31/7048* (2013.01); *A61P 33/02* (2018.01); *A61K 31/353* (2013.01)

(58) Field of Classification Search

None

See application file for complete search history.

(56) References Cited

U.S. PATENT DOCUMENTS

| | | | | |
|---|---|---|---|---|
| 4,761,404 | A | 8/1988 | Bugianesi et al. | |
| 5,763,470 | A | 6/1998 | Tang et al. | |
| 6,551,600 | B2 | 4/2003 | Hawkins et al. | |
| 6,723,710 | B2 | 4/2004 | Christianson et al. | |
| 8,618,080 | B2 | 12/2013 | Bauer et al. | |
| 9,956,240 | B2 * | 5/2018 | D'Antonio | A61K 31/7008 |
| 10,682,359 | B2 | 6/2020 | D'Antonio | |
| 2017/0145042 | A1 | 5/2017 | D'Antonio | |
| 2018/0155373 | A1 | 6/2018 | D'Antonio | |
| 2018/0280404 | A1 * | 10/2018 | D'Antonio | A61K 31/357 |

FOREIGN PATENT DOCUMENTS

| | | | |
|---|---|---|---|
| WO | WO 00/35944 | 6/2000 | |
| WO | WO-2016118191 A1 * | 7/2016 | C07H 5/04 |

OTHER PUBLICATIONS

Maley et al., Journal of Biological Chemistry, 1955, vol. 214, pp. 765-773. (Year: 1955).*

Andriani, et al. "Activity in vivo of anti-Trypanosoma cruzi compounds selected from a high throughput screening" *PLoS Negl. Trop. Dis.* 5:e1298 (2011) pp. 1-6.

Bakker, et al. "Compartmentation protects trypanosomes from the dangerous design of glycolysis" *PNAS* 97 (1999) pp. 2087-2092.

Barrett, et al. "The trypanosomiases" *Lancet* 362 (2003) pp. 1469-1480.

Bern, et al. "*Trypanosoma cruzi* and Chagas' disease in the United States" *Clin. Microbiol. Rev.* 24 (2011) pp. 655-681.

Buechner, et al. "The crystal structure of glucokinase from *Leishmania braziliensis*" *Mol. Biochem. Parasitol.* 227 (2019) pp. 47-52.

Cáceres, et al. "Molecular and biochemical characterization of hexokinase from *Trypanosoma cruzi*" *Mol. Biochem. Parasitol.* 126 (2003) pp. 251-262.

Calamini, et al. "Small Molecule Proteostasis Regulators for Protein Conformational Diseases" *Nat. Chem. Biol.* 8 (2012) pp. 185-196.

Cançado, J.R. "Long term evaluation of etiological treatment of Chagas disease with benznidazole" *Rev. Inst. Med. Trop. S. Paulo* 44 (2002) pp. 29-37.

Cazzulo, J.J. "Aerobic fermentation of glucose by trypanosomatids" *FASEB J.* 6 (1992) pp. 3153-3161.

CDC. "Neglected Parasitic Infections in the United States: Chagas Disease" *Ctrs. Dis. Contr. Prev.* (2018) pp. 1-4. http://www.cdc.gov/parasites/chagas/.

CDC. "Parasites—Leishmaniasis: Biology" *Ctrs. Dis. Contr. Prev.* (2018) p. 1. https://www.cdc.gov/parasites/leishmaniasis/biology.

Chauvlac, et al. "Crystal structure of reduced MsAcg, a putative nitroreductase from *Mycobacterium smegmatis* and a close homologue of *Mycobacterium tuberculosis* Acg" *J. Biol. Chem.* 287 (2012) pp. 44372-44383.

Cordiero, et al. "The crystal structure of *Trypanosoma cruzi* glucokinase reveals features determining oligomerization and anomer specificity of hexo-phosphorylating enzymes" *J. Mol. Biol.* 372 (2007) pp. 1215-1226.

Croft, et al. "Chemotherapy of trypanosomiases and leishmaniasis" *Trends Parasitol.* 21 (2005) pp. 508-512.

D'Abusco, et al. "A peptidyl-glucosamine derivative affects IKKα kinase activity in human chondrocytes" *Arth. Res. Ther.* 12:R18 (2010) pp. 1-11.

D'Antonio, et al. "Structure-based approach to the identification of a novel group of selective glucosamine analogue inhibitors of *Trypanosoma cruzi* glucokinase" *Mol. Biochem. Parasitol.* 204 (2015) pp. 64-76.

Doerig, C. "Protein kinases as targets for anti-parasitic chemotherapy" *Biochim. et Biophys. Acta* 1697 (2004) pp. 155-168.

Engel, et al. "Aerobic glucose fermentation by *Trypanosoma cruzi* axenic culture amastigote-like forms during growth and differentiation to epimastigotes" *Mol. Biochem. Parasitol.* 26 (1987) pp. 1-10.

(Continued)

*Primary Examiner* — Traviss C McIntosh, III

(74) *Attorney, Agent, or Firm* — Dority & Manning, PA

(57) ABSTRACT

Inhibitor compounds with biological activity against kinetoplastid parasites, along with methods of use of the compounds, are provided. The compounds can be used to strongly inhibit key drug targets found in protozoan parasites, e.g., the target *Trypanosoma cruzi* glucokinase. Compounds include derivatives of 3-nitro-2-phenyl-2H-chromene, and monosaccharide amines including D-glucosamine, D-mannosamine, D-galactosamine, and D-fructosamine.

14 Claims, 9 Drawing Sheets

(56) References Cited

OTHER PUBLICATIONS

Fatome, et al. "Radioprotective effects of $\Delta^3$-chromenes substituted in 3 by an electro-attractive group (translated)" *Eur. J. Med. Chem. Chimica Therapeutica* 11 (1976) pp. 81-82.
Gallo-Ebert, et al. "Novel Antifungal Drug Discovery Based on Targeting Pathways Regulating the Fungus-Conserved Upc2 Transcription Factor" *Antimicrob. Agent Chemother.* 58 (2014) pp. 258-266.
Habib, et al. "Catalyst-free 1, 3-dipolar cycloaddition of 3-nitrochromen with sodium azide: a facile method for the synthesis of 4-aryl-1,4-dihydrochromeno [4,3-d][1,2,3] triazole derivatives" *Tetrahedron* 65 (2009) pp. 5799-5804.
Hall, et al. "Activation of benznidazole by trypanosomal type 1 nitroreductases results in glyoxal formation" *Antimicrob. Agents Chemother.* 56 (2012) pp. 115-123.
Herwaldt, et al. "Characteristics of patients for whom benznidazole was released through the CDC-sponsered investigational new drug program for treatment of Chagas disease—United States, 2011-2018" *Morb. Mortal. Wkly. Rep.* 67 (2018) pp. 803-805.
Heussler, et al. "Hijacking of Host Cell IKK Signalosomes by the Transforming Parasite *Theileria*" *Science* 298 (2002) pp. 1033-1036.
Igoillo-Esteve, et al. "The pentose phosphate pathway in *Trypanosoma cruzi*: A potential target for the chemotherapy of Chagas disease" *Ann. Braz. Aca. Sci.* 79 (2007) pp. 649-663.
Ito, et al. "Identification of novel selective $P2Y_6$ receptor antagonists by high-throughput screening assay" *Life Sci.* 180 (2017) pp. 137-142.
Jäger, et al. (Eds.) "Trypanosomatid diseases: molecular routes to drug discovery" vol. 4 *Wiley-Blackwell* (2013) pp. 1-555.
Karlsson, et al. "Separation of monosaccharides by hydrophilic interaction chromatography with evaporative light scattering detection" *J. Chromatogr. A* 1092 (2005) pp. 246-249.
Lefebvre, et al. "Mononucleoside phosphotriester derivatives with S-acyl-2-thioethyl bioreversible phosphate-protecting groups: Intracellular delivery of 3'-azido-2',3'-dideoxythymidine 5'-monophosphate" *J. Med. Chem.* 38 (1995) pp. 3941-3950.
Lipinski, et al. "Experimental and computational approaches to estimate solubility and permeability in drug discovery and development settings" *Adv. Drug Deliv. Rev.* 46 (2001) pp. 3-26.
Lipinski, et al. "Experimental and computational approaches to estimate solubility and permeability in drug discovery and development settings" *Adv. Drug Deliv. Rev.* 23 (1997) pp. 3-25.
Lobo-Rojas, et al. "*Trypanosoma cruzi* contains two galactokinases; molecular and biochemical characterization" *Parasitol. Int'l* 65 (2016) pp. 472-482.
Luzina, et al. "Synthesis, evaluation of anticancer activity and COMPARE analysis of N-bis(trifluoromethyl)alkyl-N'-substituted ureas with pharmacophoric moieties" *Eur. J. Med. Chem.* 53 (2012) pp. 364-373.
Malo, et al. "Statistical practice in high-throughput screening data analysis" *Nat. Biotechnol.* 24 (2006) pp. 167-175.
Mao, et al. "A Novel Chromene-Based Pan-P13 Kinase Inhibitor Displays Preclinical Activity in Leukemia and Myeloma" *Blood* 112 (2008) pp. 568-569. (Abstract only).
Meija, et al. "Benznidazole-resistance in *Trypanosoma cruzi* is a readily acquired trait that can arise independently in a single population" *J. Infect. Dis.* 206 (2012) pp. 220-228.
Mercaldi, et al. "Discovery of antichagasic inhibitors by high-throughput screening with *Trypanosoma cruzi* glucokinase" *Bioorg. Med. Chem. Lett.* 29 (2019) pp. 1948-1953. (Abstract only).
Milanes, et al. "Enzymatic and structural characterization of the *Naegleria fowleri* glucokinase" *Antimicrob. Agents Chemother.* 63 (2019) pp. e02410-02418.
Rahmani-Nezhad, et al. "Synthesis, in vitro cytotoxicity and apoptosis inducing study of 2-aryl-3-nitro-2H-chromene derivatives as potent anti-breast cancer agents" *Eur. J. Med. Chem.* 86 (2014) pp. 562-569.
Rassi, et al. "Challenges and opportunities for primary, secondary, and tertiary prevention of Chagas' disease" *Heart* 95 (2009) pp. 524-534.
Ruda, et al. "Aryl phosphoramidates of 5-phospho erythronohydroxamic acid, a new class of potent trypanocidal compounds" *J. Med. Chem.* 53 (2010), pp. 6071-6078.
Ruda, et al. "Synthesis and biological evaluation of phosphate prodrugs of 4-phospho-Derythronohydroxamic acid, an inhibitor of 6-phosphogluconate dehydrogenase" *ChemMedChem*, 2 (2007) pp. 1169-1180.
Sánchez-Valdéz, et al. "Spontaneous dormancy protects *Trypanosoma cruzi* during extended drug exposure" *eLife* 7:e34039 (2018) pp. 1-20.
Stern, et al. "Structures of type B ribose 5-phosphate isomerase from Trypanosoma cruzi shed light on the determinants of sugar specificity in the structural family" *FEBS J.* 278 (2011) pp. 793-808.
Stern, et al. "Ribose 5-phosphate isomerase type B from *Trypanosoma cruzi*: kinetic properties and site-directed mutagenesis reveal information about the reaction mechanism" *Biochem. J.* 401 (2007) pp. 279-285.
Tielens, et al. "Differences in energy metabolism between trypanosomatidae" *Parasitol. Today* 14 (1998) pp. 265-271.
Urbina, et al. "Specific chemotherapy of Chagas disease: controversies and advances" *Trends Parasitol.* 19 (2003) pp. 495-501.
WHO. "Chagas disease (also known as American trypanosomiasis)" *World Health Organization* (2020) https://www.who.int/news-room/fact-sheets/detail/chagas-disease-(american-trypanosomiasis).
Wilson, et al. "Sequencing, Modeling, and Selective Inhibition of Trypanosoma brucei Hexokinase" *Chem. Bio.* 9 (2002) pp. 839-847.
Yin, et al. "Preparation of S14161 and its analogues and the discovery of 6-bromo-8-ethoxy-3-nitro-2H-chromene as a more potent antitumor agent in vitro" *Bioorg. Med. Chem. Lett.* 23 (2013) pp. 3314-3319.
Zhang, et al. "An improved method of amide synthesis using acyl chlorides" *Tetrahedron Lett.* 50 (2009) pp. 2964-2966.

* cited by examiner

1

2

3

4

5

6

7

8

9

10

11

12

13

14

15

16

17

18

23

24

25

26

27

28

29

30

31

Compound no. 13-18

Compound no. 1-6

Compound no. 7-12

MONOSACCHARIDE AMINE AND 3-NITRO-2-PHENYL-2H-CHROMENE BASED INHIBITORS OF GLUCOSE KINASES

CROSS REFERENCE TO RELATED APPLICATION

This application claims filing benefit of U.S. Provisional Patent Application Ser. No. 62/840,005, having a filing date of Apr. 29, 2019, which is incorporated herein by reference in their entirety.

BACKGROUND

Kinetoplastid parasites such as *Trypanosoma cruzi* (*T. cruzi*), *Trypanosoma brucei* (*T. brucei*), and *Leishmania* spp. utilize and depend on metabolic pathways for survival. An example of a metabolic pathway is the pentose phosphate pathway (PPP) for the production of the reducing agent NADPH and also for nucleic acid and nucleotide biosynthesis. The PPP is essential for these organisms and obstruction of the pathway leads to apoptosis. Obstruction can be caused by inhibition of the enzyme, glucose 6-phosphate dehydrogenase; for instance, by use of a drug. In order to operate successfully as a therapeutic drug, an inhibitor should selectively bind to the parasite homologue drug-target and avoid cross-reactivity with the patient's homologous enzyme (e.g., bind to the human homologous enzyme much weaker or not at all), giving rise to a good parasite selectively ratio.

*T. cruzi* is the causative agent for Chagas' disease. Benznidazole and nifurtimox are the two main clinically available treatments for Chagas' disease available in Latin America, and benznidazole has recently been accepted for use in the United States to treat Chagas' disease. Both of these drugs have the potential for resistance because they were developed over 40 years ago and alternative drugs have not emerged. *T. brucei* is the causative agent for human African sleeping sickness and various drugs are available, such as pentamidine, suramin, eflornithine, and melarsoprol. *Leishmania* spp. are protozoan parasites causing leishmaniasis and medical intervention requires treatment such as pentavalent antimony-based medicines, or more expensive treatments such as amphotericin B, miltefosine, or paromomycin. The drugs for these kinetoplastid diseases all require substantial improvements in their tolerability, safety, and efficacy.

A need exists for new drugs that strongly bind to drug targets found in these parasites. Such a need includes inhibitors of the glucose kinase enzymes, which include hexokinase and/or glucokinase. These enzymes produce the product glucose-6-phosphate (G6P), which acts as the starting substrate for the PPP. A need also exists for such inhibitors that will provide an alternative to the clinically used drugs at the present time.

SUMMARY

Objects and advantages of the invention will be set forth in part in the following description, or may be obvious from the description, or may be learned through practice of the invention.

Compounds and pharmaceutical compositions are provided that show efficacy against kinetoplastid parasites. Compounds include derivatives of scaffolds based upon 3-nitro-2-phenyl-2H-chromene and scaffolds based upon monosaccharide amines including hexosamines (e.g., glucosamine, galactosamine, mannosamine) and fructosamines.

Methods are also generally provided for treating a subject that is infected by a kinetoplastid parasite, including *T. cruzi, T. brucei*, and *Leishmania* spp. by administering to the subject a pharmaceutical composition that includes a compound as disclosed.

Other features and aspects of the present invention are discussed in greater detail below.

BRIEF DESCRIPTION OF THE DRAWINGS

A full and enabling disclosure of the present subject matter, including the best mode thereof to one of ordinary skill in the art, is set forth more particularly in the remainder of the specification, including reference to the accompanying figures in which.

DETAILED DESCRIPTION

Figure 1:
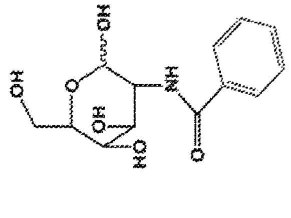
FIG. 1 provides structures for monosaccharide amine-based compound nos. 1-18 as disclosed herein.
Figure 1:
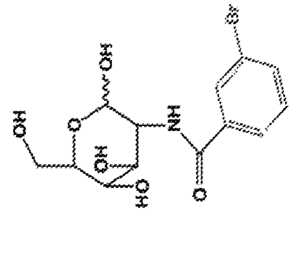
Figure 1:
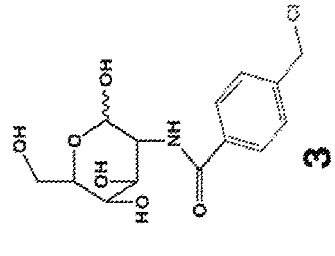
Figure 1:
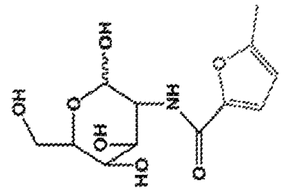
Figure 1:
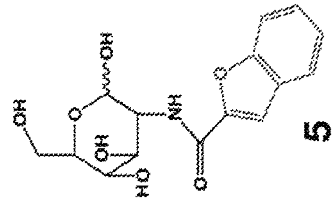
Figure 1:
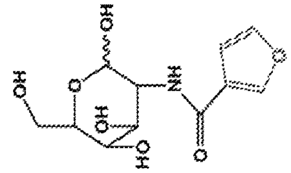
Figure 1:
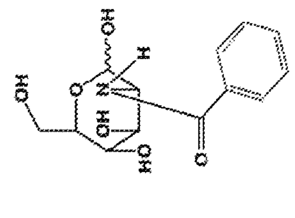
Figure 1:
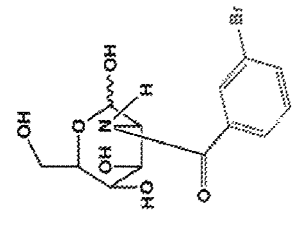
Figure 1:
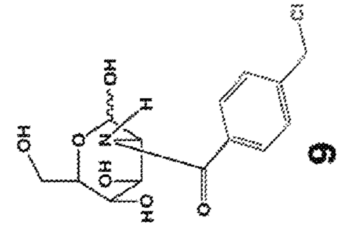
Figure 1:
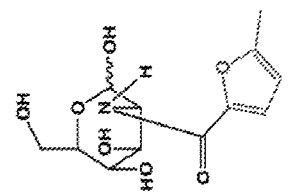
Figure 1:
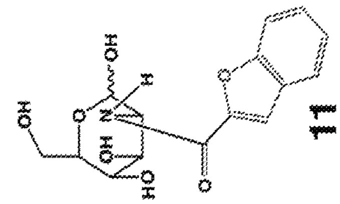
Figure 1:
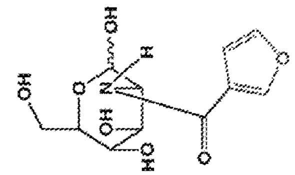
Figure 1:
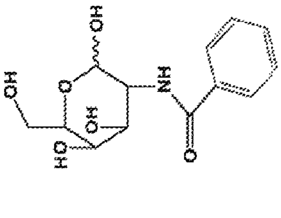
Figure 1:
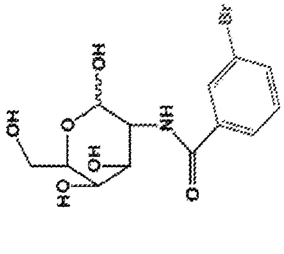
Figure 1:
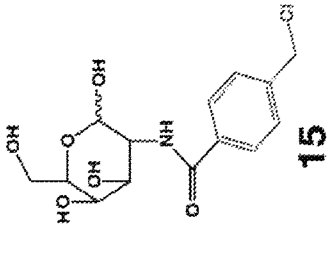
Figure 1:
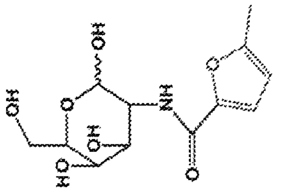
Figure 1:
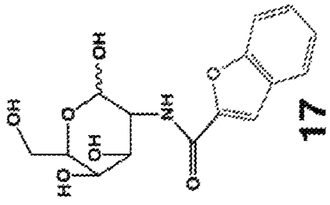
Figure 1:
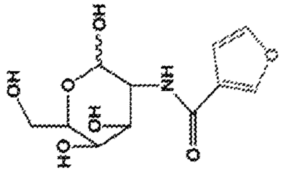

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield a still further embodiment. Thus, it is intended that the present invention cover such modifications and variations as come within the scope of the appended claims and their equivalents. It is to be understood by one of ordinary skill in the art that the present discussion is a description of exemplary embodiments only and is not intended as limiting the broader aspects of the present invention, which broader aspects are embodied exemplary constructions.

Compounds, compositions, and methods are generally provided that can be used against targets, e.g., *Trypanosoma cruzi* glucokinase (TcGlcK), that are found in protozoan parasites, and in particular, in kinetoplastid parasites. The compounds may serve as viable substitutes for currently used drugs in clinical settings or may be used in conjunction with currently used drugs. The compounds described herein include experimentally confirmed potent inhibitors of TcGlcK and *Leishmania braziliensis* glucokinase (LbGlcK), and may also be potent inhibitors of *T. cruzi* hexokinase, *T. brucei* glucokinase, *T. brucei* hexokinase, as well as *L. braziliensis* hexokinase. The drug compounds described herein may offer an alternative to the mainstream drugs that are used in the clinic for diseases of the trypanosome, such as American Trypanosomiasis (Chagas' disease), Human African Trypanosomiasis (Human African Sleeping Sickness), and Leishmaniasis, which are caused by parasites *T. cruzi, T. brucei*, and *Leishmania* spp., respectively.

In one embodiment, disclosed compounds are derivatives of a monosaccharide amine such as a hexosamine having the structure of:

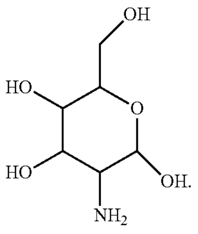

For instance, a compound can be a derivative of, without limitation, glucosamine:

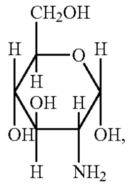

mannosamine:

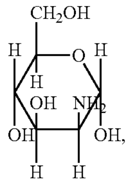

or galactosamine:

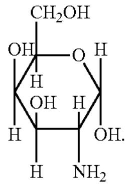

A compound can optionally be a derivative of a fructosamine in either the pyranose form or the furanose form, e.g., pyranose form:

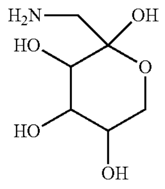 [SMILES: NCC1(O)OCC(O)C(O)C1O]

furanose form:

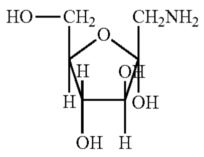

For instance, a compound can be a derivative of, without limitation,

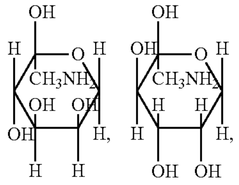

etc.

Compounds disclosed herein based upon the monosaccharide amine scaffolds include derivatizations on the amine group of the scaffolds. For instance, monosaccharide amine-based compounds can include an amine group having the following structure:

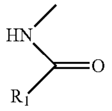

in which $R_1$ can include an aromatic organic group or a halogenated aromatic group, including, without limitation, a benzene group, a benzene-derivative group (e.g., a phenol group, a toluene group, an aniline group, a heterocycle group such as pyridine, etc.), a polycyclic aromatic group (e.g., a naphthalene group, etc.) or their derivatives (e.g., a benzothiophene group, a benzofuran group, an indole group, an indazole group, a benzothiazole group, etc.), any of which can optionally include a halogen or C1-C6 alkyl halogen.

In one embodiment, disclosed compounds can include a benzene-based derivative at the amine group of the scaffold. For instance, the amine group of a monosaccharide amine can have the following structure:

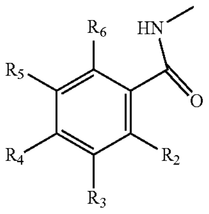

In which $R_2$, $R_3$, $R_4$, $R_5$, and $R_6$ are independently selected from hydrogen, halogen (F, Cl, Br, I) and C1-C6 alkyl halogen. In one embodiment, at least one of $R_2$, $R_3$, $R_4$, $R_5$, and $R_6$ are halogen or C1-C6 alkyl halogen.

Representative derivatization groups include, without limitation benzene, halobenzene, or (halomethyl)benzene, examples of which include, without limitation:

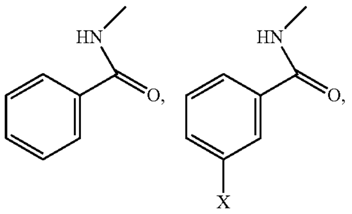

-continued

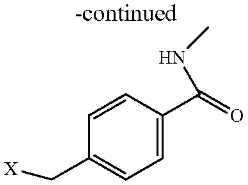

in which X is F, Cl, Br, or I.

FIG. 1 includes several examples of monosaccharide amine-based compounds including glucosamine-based compounds (compound nos. 1, 2, 3 on FIG. 1), mannosamine-based compounds (compound nos. 7, 8, 9 on FIG. 1), and galactosamine-based compounds (compound nos. 13, 14, 15 on FIG. 1).

In one embodiment, a monosaccharide amine-based compound can include a furan-based derivatization including furan, alkyllfuran, or benzofuran in which the furan-based group makes connection via the C2 or the C3 of the furan group. By way of example, a furan-based derivatization can have a structure including, without limitation:

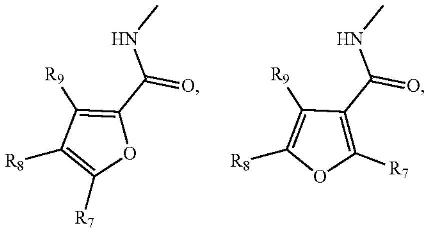

or

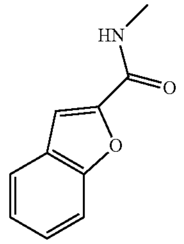

in which $R_7$, $R_8$, and $R_9$ are independently selected from hydrogen, C1-C6 alkyl, and any of the halogens (e.g., F, Cl, Br, or I).

FIG. 1 includes several examples of this type of derivatization group including glucosamine-based compounds (compound nos. 4, 5, 6 on FIG. 1), mannosamine-based compounds (compound nos. 10, 11, 12 on FIG. 1), and galactosamine-based compounds (compound nos. 16, 17, 18 on FIG. 1).

In one embodiment, disclosed inhibitors are based upon 3-nitro-2-phenyl-2H-chromene, which has the following structure:

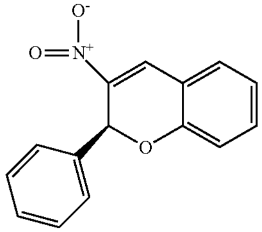 [SMILES: O=[N+]([O-])C1=Cc2ccccc2O[C@H]1c1ccccc1]

3-nitro-2-phenyl-2H-chromene inhibitors can generally have the following structure:

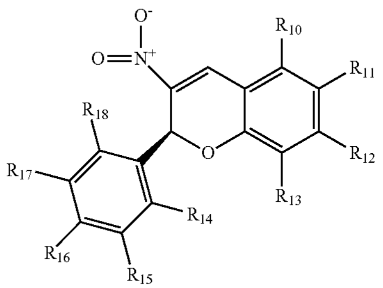

in which $R_{10}$, $R_{11}$, $R_{12}$, $R_{13}$, $R_{14}$, $R_{15}$, $R_{16}$, $R_{17}$, and $R_{18}$ are independently selected from hydrogen, halogen, C1-C4 alkyl halogen, C1-C4 alkyl, C1-C4 alkoxy, or any two adjacent of which are components of a ring fused to the respective aryl group including conjugated and non-conjugated rings, including heterocyclic rings and derivatized rings derivatized with one or more of hydrogen, halogen, C1-C4 alkyl halogen, C1-C4 alkyl, C1-C4 alkoxy, and in which at least one of $R_{14}$ and $R_{18}$ includes a halogen.

In one embodiment, 3-nitro-2-phenyl-2H-chromene-based inhibitors can include those of the above structure in which at least one of $R_{14}$ and $R_{18}$ includes a halogen and:

$R_{10}$, $R_{11}$, $R_{12}$, $R_{13}$, are independently selected from hydrogen, halogen, or any two adjacent of which are components of a conjugated ring fused to the aryl group, and $R_{15}$, $R_{16}$, $R_{17}$ are independently selected from hydrogen, C1-C4 alkoxy, or any two adjacent of which are components of a conjugated or non-conjugated ring fused to the aryl group in which the ring can optionally be a heterocyclic ring.

Specific examples of 3-nitro-2-phenyl-2H-chromene inhibitors include the following, without limitation:

19

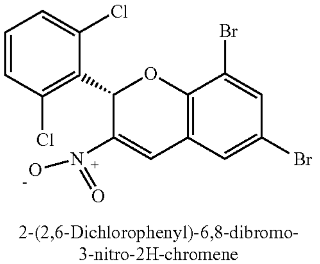

2-(2,6-Dichlorophenyl)-6,8-dibromo-3-nitro-2H-chromene

20

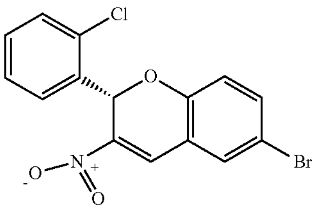

6-Bromo-2-(2-chlorophenyl)-3-nitro-2H-chromene

-continued

21

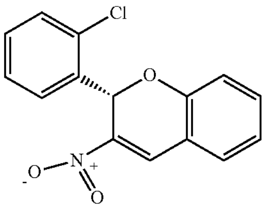

2-(2-Chlorophenyl)-3-nitro-2H-chromene

22

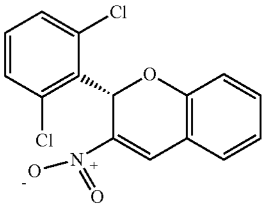

2-(2,6-Dichlorophenyl)-3-nitro-2H-chromene

Figure 2:
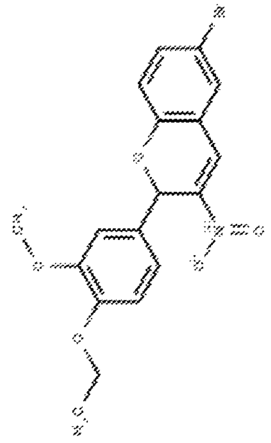
FIG. 2 provides structures for 3-nitro-2-phenyl-2H-chromene-based compounds no. 23-31 as disclosed herein.
Figure 2:
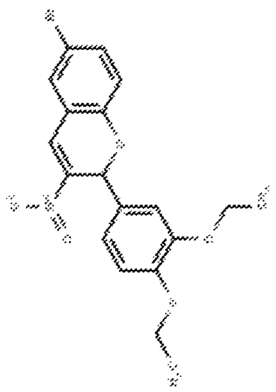
Figure 2:
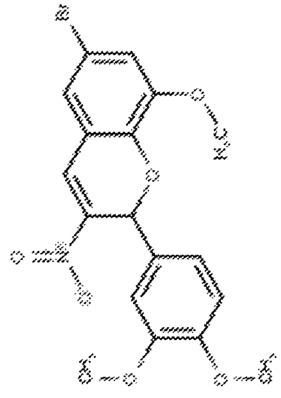
Figure 2:
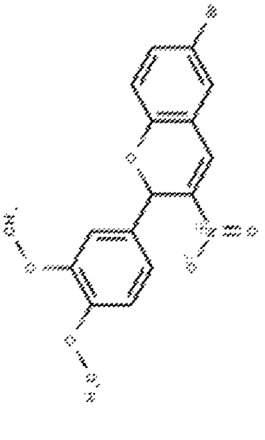
Figure 2:
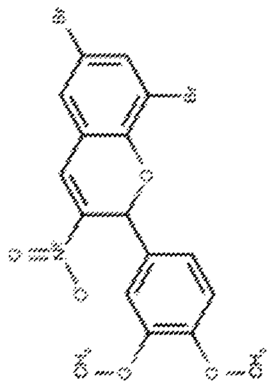
Figure 2:
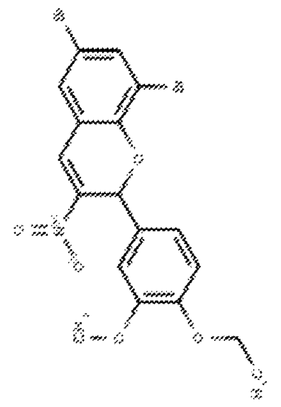
Figure 2:
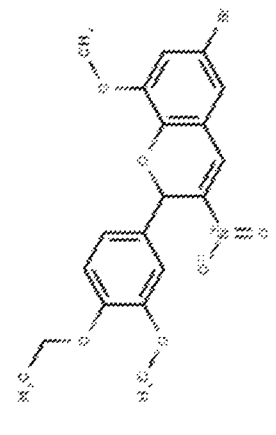
Figure 2:
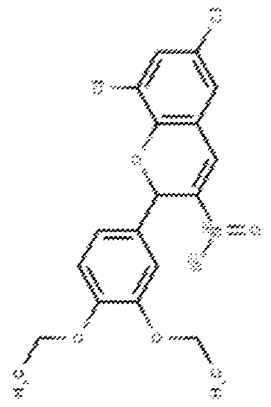
Figure 2:
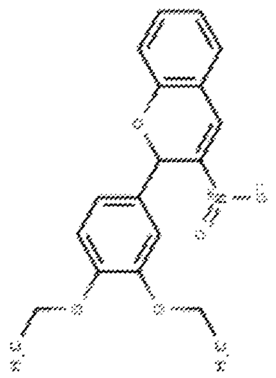

Additional examples of 3-nitro-2-phenyl-2H-chromene based inhibitors are provided in FIG. 2 including 6-Bromo-2-(4-ethoxy-3-methoxyphenyl)-3-nitro-2H-chromene (compound no. 23), 6-Bromo-2-(3,4-diethoxyphenyl)-3-nitro-2H-chromene (compound no. 24), 6-Bromo-2-(3,4-dimethoxyphenyl)-8-methoxy-3-nitro-2H-chromene (compound no. 25), 6-Bromo-2-(3,4-dimethoxyphenyl)-3-nitro-2H-chromene (compound no. 26), 6,8-Dibromo-2-(3,4-dimethoxyphenyl)-3-nitro-2H-chromene (compound no. 27), 6,8-Dibromo-2-(4-ethoxy-3-methoxyphenyl)-3-nitro-2H-chromene (compound no. 28), 6-Bromo-2-(4-ethoxy-3-methoxyphenyl)-8-methoxy-3-nitro-2H-chromene (compound no. 29), 6,8-Dichloro-2-(3,4-diethoxyphenyl)-3-nitro-2H-chromene (compound no. 30), 2-(3,4-Diethoxyphenyl)-3-nitro-2H-chromene (compound no. 31).

According to one embodiment, pharmaceutical compositions are disclosed that include a pharmaceutically acceptable carrier and at least one compound as disclosed herein in a pharmaceutically effective amount. In one embodiment, a pharmaceutical composition can incorporate one of the compounds illustrated in FIG. 1 and FIG. 2.

The term "pharmaceutically effective amount" refers to the amount of a drug or pharmaceutical agent that will elicit the biological or medical response of a tissue, system, animal, or human that is being sought by a researcher or clinician. This amount can be a therapeutically effective amount.

The term "pharmaceutically acceptable carrier" is used herein to refer to a carrier that is useful in preparing a pharmaceutical composition that is generally safe, non-toxic and neither biologically nor otherwise-undesirable, and is acceptable for veterinary use as well as human pharmaceutical use. A "pharmaceutically acceptable carrier" as used in the specification and claims can include both one and more than one such carrier. By "pharmaceutically acceptable" it is meant the carrier must be compatible with the other ingredients of the formulation and not deleterious to the recipient thereof.

Pharmaceutical compositions may be prepared by any of the methods well known in the art of pharmacy. Pharmaceutical compositions encompass any compositions made by admixing the active ingredients and a pharmaceutically acceptable carrier. The carrier may take a wide variety of forms depending on the form of preparation desired for administration, e.g., oral or parenteral (including intravenous).

The terms "administration of" or "administering a" pharmaceutical composition should be understood to mean providing a pharmaceutical composition to an individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

Thus, the pharmaceutical composition can be presented as discrete units suitable for oral administration such as capsules, cachets, or tablets each containing a predetermined amount of the active ingredients. Further, the composition can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the composition may also be administered by controlled-release means and/or delivery devices. The foregoing list is illustrative only and is not intended to be limiting in any way.

Pharmaceutical compositions intended for oral use may contain one or more agents selected from the group consisting of sweetening agents, flavoring agents, coloring agents and preserving agents in order to provide pharmaceutically elegant and palatable preparations. Tablets may contain a composition having at least one of the compounds described herein in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid, or talc. The tablets may be uncoated or they may be coated by known techniques to delay disintegration and absorption in the gastrointestinal tract and thereby provide a sustained action over a longer period. A tablet may be prepared by compression or molding, optionally with one or more accessory ingredients or adjuvants. Compressed tablets may be prepared by compressing, in a suitable machine, at least one of disclosed compounds in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent.

Pharmaceutical compositions for oral use may also be presented as hard gelatin capsules wherein one or more of the disclosed compounds is mixed with an inert solid diluent, for example, calcium carbonate, calcium phosphate or kaolin, or as soft gelatin capsules wherein the compound(s) is/are mixed with water or an oil medium, for example peanut oil, liquid paraffin, or olive oil.

Pharmaceutical compositions can also include aqueous suspensions, which contain the active materials in admixture with excipients suitable for the manufacture of aqueous suspensions. In addition, oily suspensions may be formulated by suspending at least one of the disclosed compounds in a vegetable oil, for example arachis oil, olive oil, sesame oil or coconut oil, or in a mineral oil such as liquid paraffin. Oily suspensions may also contain various excipients. The pharmaceutical composition may also be in the form of oil-in-water emulsions, which may also contain excipients such as sweetening and flavoring agents.

Pharmaceutical compositions can be in the form of a sterile injectable aqueous or oleaginous suspension, or in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage, and should be preserved against the contaminating action of microorganisms such as bacteria and fungi.

Pharmaceutical compositions can be in a form suitable for topical use such as, for example, an aerosol, cream, ointment, lotion, dusting powder, or the like. Further, the compositions can be in a form suitable for use in transdermal devices. These formulations may be prepared via conventional processing methods. As an example, a cream or ointment can be prepared by mixing hydrophilic material and water, together with about 5 wt. % to about 10 wt. % of one or more of the disclosed compound, to produce a cream or ointment having a desired consistency.

Pharmaceutical compositions can also be in a form suitable for rectal administration wherein the carrier is a solid. Suitable carriers include cocoa butter and other materials commonly used in the art.

Methods are also provided for inhibiting glucokinase and/or hexokinase, both in vitro and in vivo. In one embodiment, the method comprises contacting the glucokinase and/or hexokinase with at least one of the disclosed compounds, and in one embodiment, one of the compounds illustrated above, i.e., a compound having a structure as described above for any of compounds 1-31.

For instance, a method is provided for inhibiting glucokinase and/or hexokinase; for instance, inhibiting the enzyme in a parasitic organism. This method comprises locating a compound as described or a composition including a compound as described in an area that includes the glucokinase and/or the hexokinase. For instance, a method can include administering to the parasitic organism a composition comprising a pharmaceutically acceptable carrier and at least one compound as described herein and having one of structures 1-31. The parasitic organism can be a parasite that contains glucokinase and/or hexokinase or can be an organism that carries the parasite. The parasitic organism can be a cause of a disease associated with the parasite. Such diseases include American Trypanosomiasis (Chagas' disease), Human African Trypanosomiasis (African Sleeping Sickness), Leishmaniasis, Malaria, Schistosomiasis (Snail Fever), Filarial diseases, etc.

Also, a method is provided for treating a mammal that is infected by a parasite or parasitic organism. This method comprises administering to the disease-affected mammal a composition comprising a pharmaceutically acceptable carrier and at least one compound as described herein, and in one embodiment, a compound having one of structures 1-31. Examples of such disease-affected mammals include humans and domestic animals (e.g., dogs, cats, and thereof).

The term "treatment" or "treating" means any administration of a pharmaceutical composition to obtain a desired pharmacologic and/or physiologic effect. The effect may be prophylactic in terms of completely or partially preventing a disease or symptom thereof, and/or may be therapeutic in terms of a partial or complete cure for a disease and/or adverse effect attributable to the disease. Treatment includes (a) inhibiting the disease in the subject that is experiencing or displaying the pathology or symptomatology of the diseased (i.e., arresting further development of the pathology and/or symptomatology), or (b) ameliorating the disease in the subject that is experiencing or displaying the pathology or symptomatology of the diseased (i.e., reversing the pathology and/or symptomatology).

The present disclosure may be better understood with reference to the Examples, set forth below.

Example 1

Figure 3:
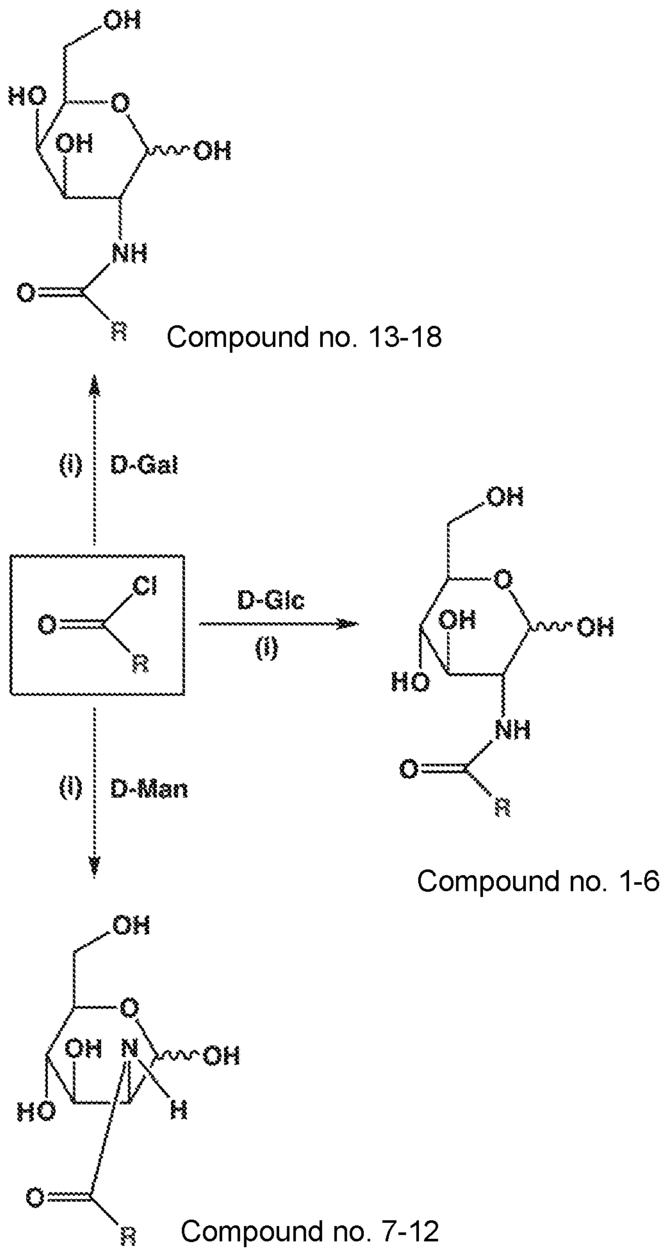
FIG. 3 schematically illustrates a synthesis approach used in forming monosaccharide-based inhibitors described herein.

The eighteen compounds illustrated in FIG. 1 were synthesized, purified, and fully characterized by $^1$H-NMR, $^{13}$C-NMR, and HRMS. The synthesis of each compound involved a one-step hydrolysis reaction of one of six different acyl chloride derivatives with D-glucosamine, D-mannosamine, and D-galactosamine. FIG. 3 provides a general synthesis approach used in forming the compounds. Conditions: (i) triethylamine (TEA), $K_3PO_4$, 30 minutes, room temperature. Each compound was purified through high-performance liquid chromatography (HPLC). A TSKgel® Amide-80 column was selected based on its ability to separate similar monosaccharides.

In order to determine if TcGlcK and HsHxKIV exhibited a broad substrate range, common monosaccharides were tested for TcGlcK activity that included the substrates, D-galactose, D-mannose, and D-fructose. D-Glucose was also tested as a control with alternative substrates. The protein expression work for TcGlcK and HsHxKIV were each made possible through the *E. coli* strain BL21(DE3) system. Purification of each enzyme was performed through cobalt-NTA chromatography followed by size-exclusion chromatography; assessment of purity was performed by SDS-PAGE. In enzymatic assays, a time-optimum ($T_{OPT}$) was determined to be 120 seconds for TcGlcK and 600 seconds for HsHxKIV; all assays were run at room temperature. A general reaction scheme included a first reaction in which the monosaccharide, ATP, and $Mg^{2+}$ react with the enzyme, e.g., TcGlcK, forming a hexose-phosphate and ADP. In a second reaction, hexose-phosphate with the assistance of glucose-6-phosphate dehydrogenase (G6PDH) and $NADP^+$ was converted to the lactone form of the hexose-phosphate and NADPH. Fluorescence of NADPH was monitored using a fluorescence microplate reader with emission and excitation wavelengths of 340 nm and 485 nm, respectively.

Figure 4:
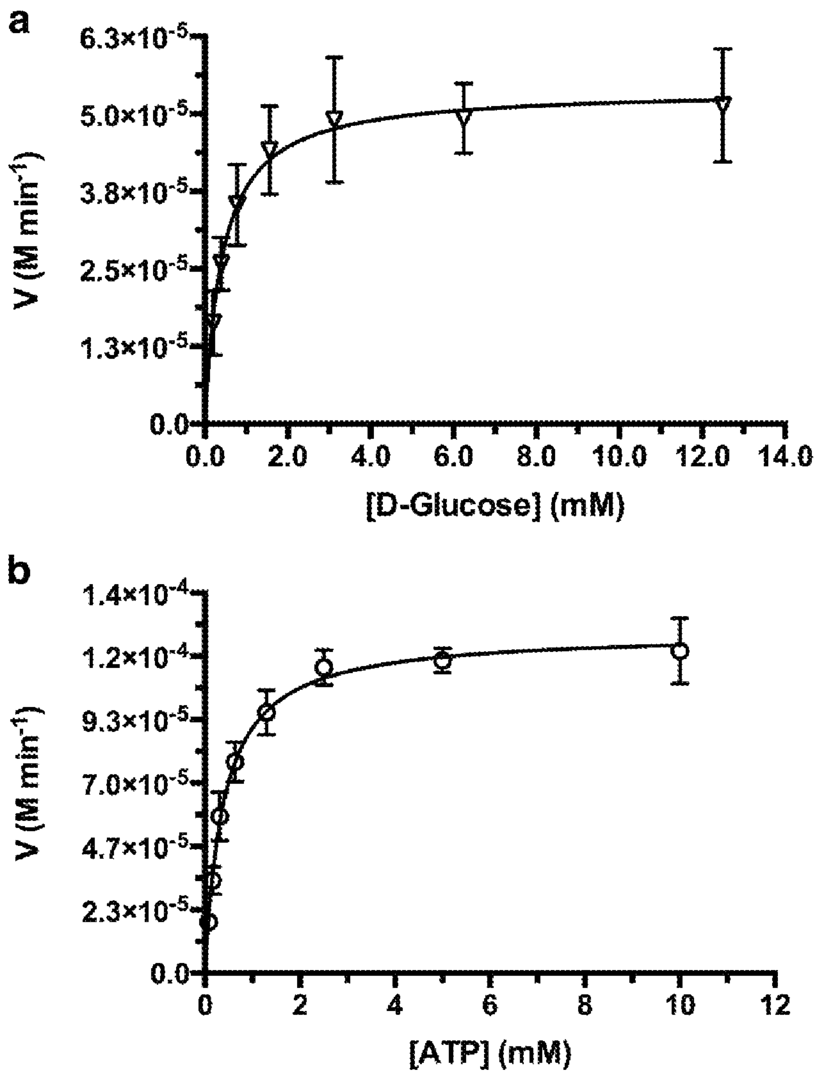
FIG. 4 is a Michaelis-Menten enzyme kinetic plot for a D-glucose TcGlcK assay performed in triplicate.
Figure 5:
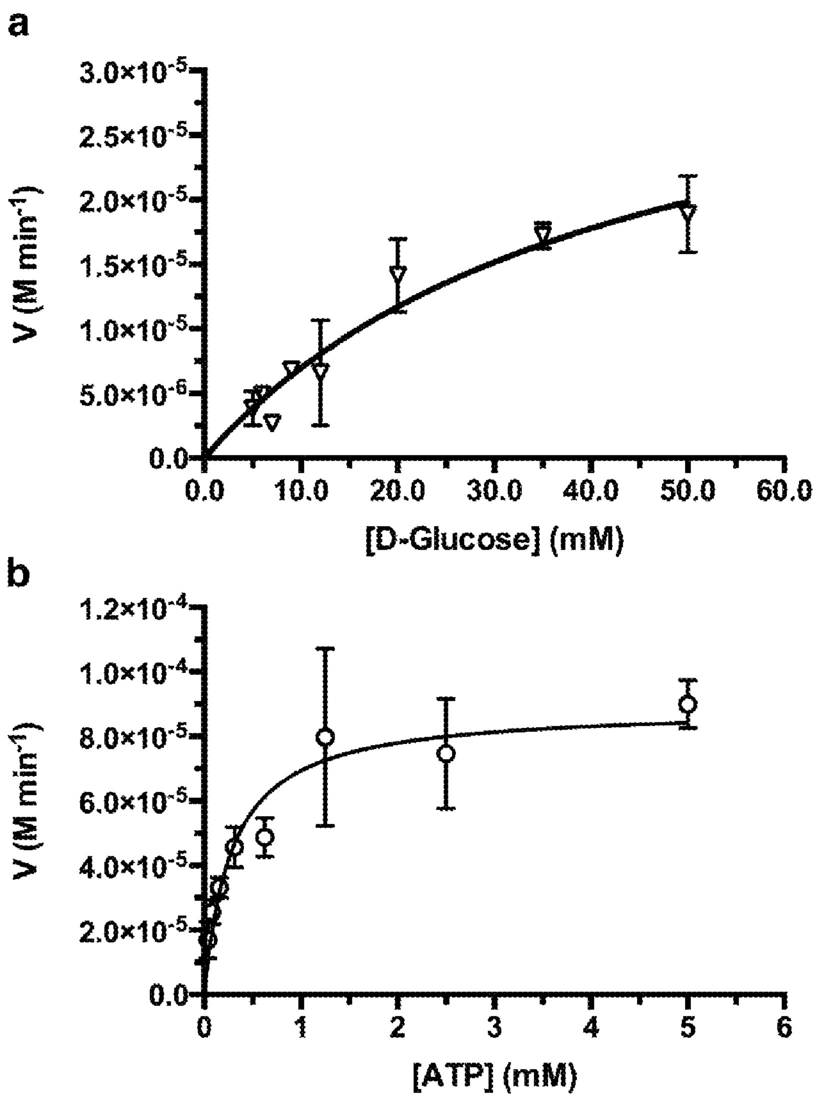
FIG. 5 is a Michaelis-Menten enzyme kinetic plot for a D-glucose *Homo sapiens* hexokinase IV (HsHxKIV) assay performed in triplicate.

FIG. 4 and FIG. 5 present typical Michaelis-Menten enzyme kinetic plots for D-glucose. As shown, the $NADP^+$ to NADPH turnover rate is a function of [D-glucose] & [ATP] for TcGlcK (FIG. 4) and HsHxKIV (FIG. 5) absent inhibition. Michaelis-Menten constant ($K_M$) values, which were used as the set final assay concentrations of substrates D-glucose and ATP for the primary screens, were determined for both TcGlcK and HsHxKIV in triplicate runs. The $K_M$ values for TcGlcK with respect to D-glucose and ATP were 0.40 mM and 0.34 mM, respectively. The $K_M$ values for HsHxKIV with respect to D-glucose and ATP were 43 mM and 0.20 mM, respectively.

The results of the primary assay screen for TcGlcK are provided in Table 1, below. As control, a known potent TcGlcK inhibitor carboxybenzyl glucosamine (CBZ-GlcN) described in U.S. Pat. No. 9,956,240 to D'Antonio et al., which is incorporated herein by reference, was utilized. CBZ-GlcN exhibited an inhibition level of 92%. CBZ-GlcN has the following structure:

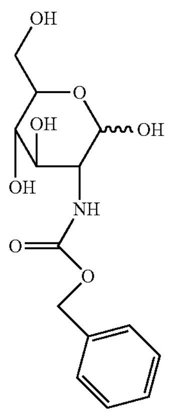

As indicated in Table 1 below, the enzyme—inhibition screening assay (N=1) showed that most of the compounds had substantial inhibition against TcGlcK at compound concentrations of 20 µM. As indicated, compound 11 revealed the lowest level of inhibition and the 27% level of compound 15 was designated as a cutoff percentage. The cutoff percentage was calculated by using normalized percent inhibition that took into consideration the positive and negative controls of the fluorescence readout from a fluorescence microplate reader. In addition, an unconfirmed hit was selected if the activity measurement was three standard deviations away from the mean of the positive controls.

TABLE 1

| Compound no. | TcGlcK Inh20 (%) |
|---|---|
| 1 | 65 |
| 2 | 57 |
| 3 | 42 |
| 4 | 51 |
| 5 | 31 |
| 6 | 51 |
| 7 | 71 |
| 8 | 35 |
| 9 | 33 |
| 10 | 56 |
| 11 | 10 |
| 12 | 58 |
| 13 | 59 |
| 14 | 31 |
| 15 | 27 |
| 16 | 30 |
| 17 | 39 |
| 18 | 56 |

The 16 compounds showing substantial inhibition against TcGlcK at compound concentrations of 20 µM were then examined in a confirmatory assay in which the amino sugar analogues were at a concentration of 20 µM and were tested against the assay's only coupling enzyme, G6PDH, to verify enzyme activity; the assay was performed in quadruplicate. Since none of the compounds inhibited G6PDH by more than 20%, they all proceeded as on-target confirmed hits (Table 2). These confirmed hits included representatives from all three monosaccharide scaffolds tested (i.e., D-GlcN, D-ManN, and D-GalN).

TABLE 2

| Compound no. | G6PDH Inh20 (%) |
|---|---|
| 1 | 0.5 ± 1.0 |
| 2 | 0.0 ± 0.0 |
| 3 | 0.0 ± 0.0 |
| 4 | 0.3 ± 0.5 |
| 5 | 0.0 ± 0.0 |
| 6 | 0.0 ± 0.0 |
| 7 | 0.0 ± 0.0 |
| 8 | 0.0 ± 0.0 |
| 9 | 0.0 ± 0.0 |
| 10 | 0.0 ± 0.0 |
| 12 | 0.0 ± 0.0 |
| 13 | 0.0 ± 0.0 |
| 14 | 0.0 ± 0.0 |
| 16 | 0.0 ± 0.0 |
| 17 | 0.0 ± 0.0 |
| 18 | 0.0 ± 0.0 |

As indicated in Table 3, below, the enzyme-inhibition screening assay (N=1) for HsHxKIV and the 18 compounds of FIG. 1 showed relatively low inhibition for 4 of the 18 compounds with percent inhibition being less than 30% when compound concentrations were set as 20 μM. None of the inhibitor compounds inhibited HsHxKIV to a magnitude greater than 55%.

TABLE 3

| Compound no. | HsHxKIV Inh20(%) |
|---|---|
| 1 | 39 |
| 2 | 31 |
| 3 | 35 |
| 4 | 26 |
| 5 | 25 |
| 6 | 41 |
| 7 | 55 |
| 8 | 27 |
| 9 | 28 |
| 10 | 49 |
| 11 | 12 |
| 12 | 32 |
| 13 | 38 |
| 14 | 30 |
| 15 | 8 |
| 16 | 41 |
| 17 | 37 |
| 18 | 47 |

In general, through a qualitative assessment, the confirmed hits did not appear to be that selective for TcGlcK. The most selective of the group was compound 4 that showed a TcGlcK Inh20:HsHxKIV Inh20 ratio of 1.91 (higher values of this ratio would indicate a more selective inhibitor towards TcGlcK). By using the same analysis, BENZ-GlcN (compound 1) had a ratio of 1.65 and CBZ-GlcN had a ratio of 45.9.

Compounds were further screened against the *T. cruzi* (Tulahuen strain) infective form (trypomastigote and amastigote life stages) co-cultured in NIH-3T3 fibroblasts to establish $IC_{50}$ values. Assays were performed in triplicate.

The single dose in vitro study included administration of the compounds in 80 μM inhibitor concentrations (N=3). Amphotericin B was used as a control. The *T. cruzi* in vitro assays revealed good biological activity for the compounds tested, which highlights on importance of TcGlcK as a potential drug-target for the parasite. Results are shown in Table 4, below. For comparison, literature values for CBZ-GlcN $IC_{50}$ are 48.73±0.69 μM and for benznidazole are 1.12±0.010 μM. The Amphotericin B average value from 6 replicates was 1.08±0.84 μM.

TABLE 4

| Compound no. | *T. cruzi* $IC_{50}$ (μM) |
|---|---|
| 1 | 16.08 ± 0.16 |
| 2 | 66.17 ± 3.83 |
| 3 | 52.91 ± 2.72 |
| 4 | >80 |
| 5 | 27.24 ± 3.74 |
| 6 | 49.89 ± 2.99 |
| 7 | 43.53 ± 0.68 |
| 8 | 38.37 ± 1.40 |
| 9 | 38.37 ± 1.41 |
| 10 | >80 |
| 11 | 42.50 ± 6.50 |
| 12 | 67.53 ± 1.75 |
| 13 | 55.29 ± 11.92 |
| 14 | 19.93 ± 3.28 |
| 15 | 37.89 ± 4.77 |
| 16 | 20.25 ± 2.53 |
| 17 | 66.57 ± 13.66 |
| 18 | 36.38 ± 1.47 |

A threshold value of 28 μM for $IC_{50}$ was implemented so that compounds could be excluded from consideration to narrow down to the top 4 hits. The final four front-runner hits were compounds 1, 5, 14, and 16 and a summary of properties is shown in Tables 5 and 6.

TABLE 5

| Compound | TcGlcK $K_i$ (μM)[a] | TcGlcK Inh20 (%)[b] | *T. cruzi* $IC_{50}$ (μM)[c] | Amino sugar moiety |
|---|---|---|---|---|
| 1 | 32 ± 26[d] | 64.7 | 16.08 ± 0.16[d] | D-glucosamine |
| 5 | 139 ± 35 | 31.2 | 27.24 ± 3.74 | D-glucosamine |
| 14 | nd[e] | 30.8 | 19.93 ± 3.28 | D-galactosamine |
| 16 | nd[e] | 30.0 | 20.25 ± 2.53 | D-galactosamine |

[a]TcGLCK - inhibitor $K_i$ value determinations; number of replicates, N = 3

[b]Inh20, percentage of inhibition at 20 μM of the compound in comparison to controls; number of replicates, N = 1

[c]In vitro *T. cruzi* (Taluhuen strain) infective form growth inhibition in NIH-3T3 fibroblasts; number of replicates, N = 3

[d]D'Antonio, et al (2015) Mol. Biochem. Parasitol. 204, 64-76.

[e]Not determined

TABLE 6

| ID # | Mol. formula (# atoms) | MW (g/mol) | CLogP[b] | H-bond donor | H-bond acceptor | Lipinski Score[c] | MR[b] ($cm^3$/mol) | PSA[b] (Å) |
|---|---|---|---|---|---|---|---|---|
| 1 | $C_{13}H_{17}NO_6$(37) | 283.28 | −0.4686 | 5 | 7 | 4 | 68.00 | 119.25 |
| 5 | $C_{15}H_{17}NO_7$(41) | 323.30 | 0.0914 | 5 | 8 | 4 | 76.74 | 128.48 |
| 14 | $C_{13}H_{16}BrNO_6$(37) | 362.17 | 0.5960 | 5 | 7 | 4 | 75.69 | 119.25 |
| 16 | $C_{12}H_{17}NO_7$(37) | 287.27 | −0.7936 | 5 | 8 | 4 | 65.47 | 128.48 |

[a]MW is molecular weight; MR is molar refractivity; and PSA is polar surface area.
[b]Calculated using ChemDraw Ultra (version 12.0).
[c]Lipinski's Rule of Five; score is out of 4; refer to Refs. (23-25).

Figure 6:
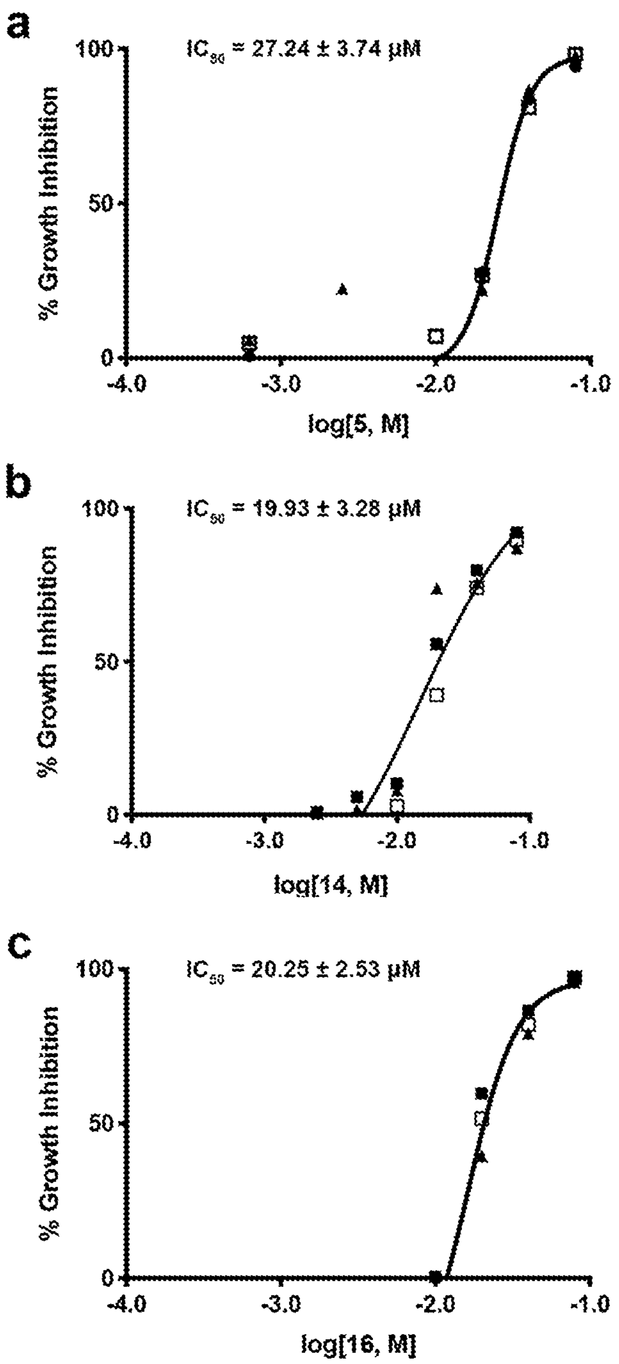
FIG. 6 presents the dose response of (a) compound no. 5 activity, (b) compound no. 14 activity, and (c) compound no. 16 activity on *T. cruzi* (Tulahuen strain) intracellular amastigote growth inhibition in NIH-3T3 fibroblasts. The curve and the $IC_{50}$ were calculated from measurements determined in triplicate and expressed as percent growth inhibition of the *T. cruzi* parasite infection of mammalian cells.
Figure 7:
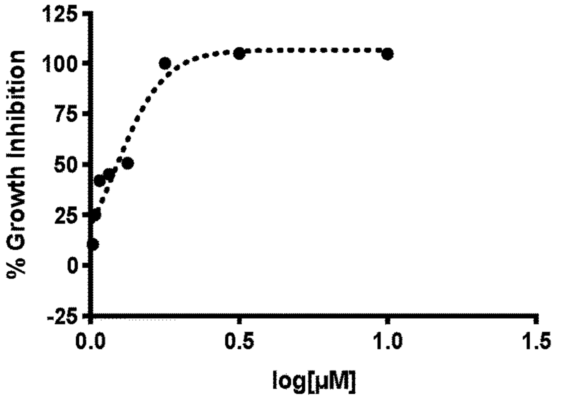
FIG. 7 presents the activity curve for a 3-nitro-2-phenyl-2H-chromene-based compound (compound no. 19) against *T. brucei.*
Figure 8:
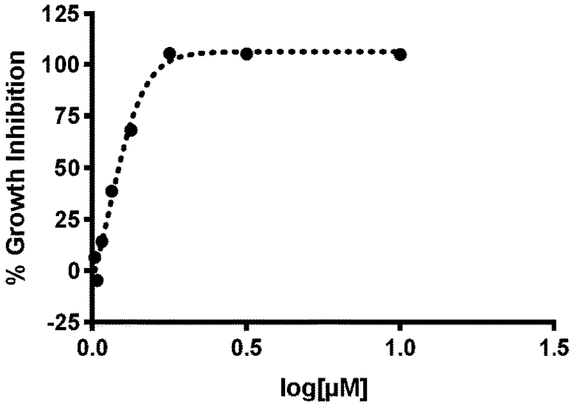
FIG. 8 presents the activity curve for a 3-nitro-2-phenyl-2H-chromene-based compound (compound no. 20) against *T. brucei.*
Figure 9:
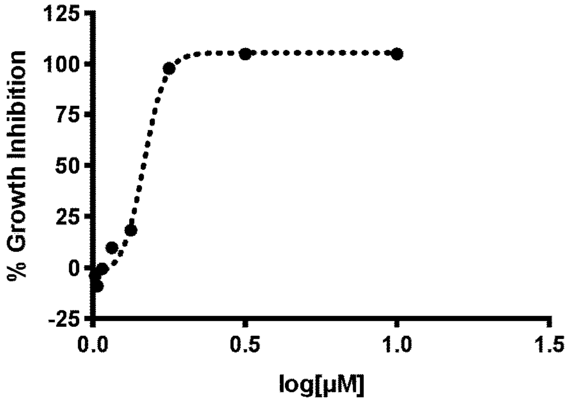
FIG. 9 presents the activity curve for a 3-nitro-2-phenyl-2H-chromene-based compound (compound no. 21) against *T. brucei.*
Figure 10:
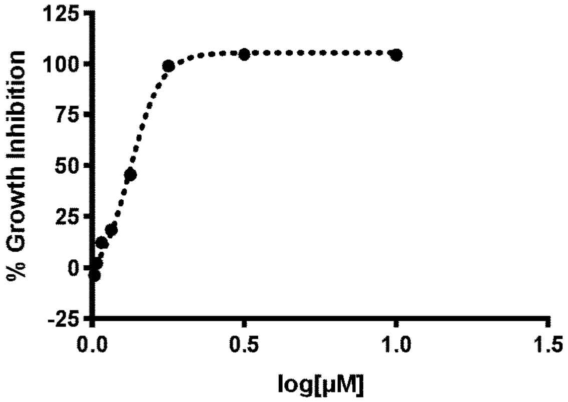
FIG. 10 presents the activity curve for a 3-nitro-2-phenyl-2H-chromene-based compound (compound no. 22) against *T. brucei.*
Figure 11:
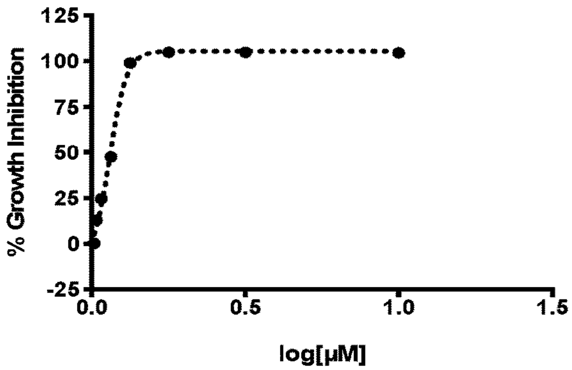
FIG. 11 presents the activity curve for a 3-nitro-2-phenyl-2H-chromene-based compound (compound no. 23) against *T. brucei.*
Figure 12:
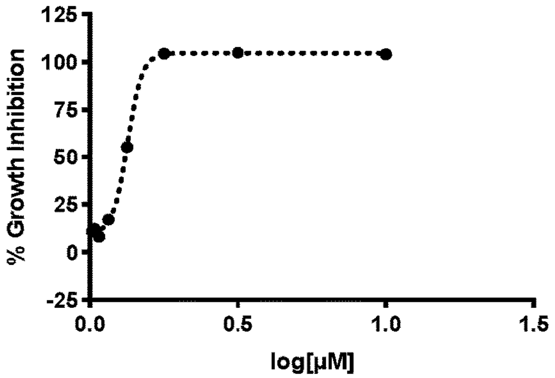
FIG. 12 presents the activity curve for a 3-nitro-2-phenyl-2H-chromene-based compound (compound no. 24) against *T. brucei.*
Figure 13:
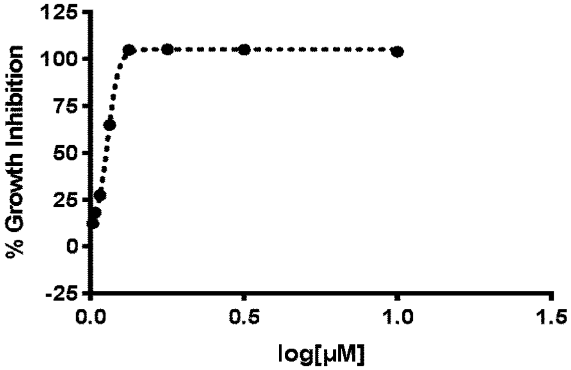
FIG. 13 presents the activity curve for a 3-nitro-2-phenyl-2H-chromene-based compound (compound no. 25) against *T. brucei.*
Figure 14:
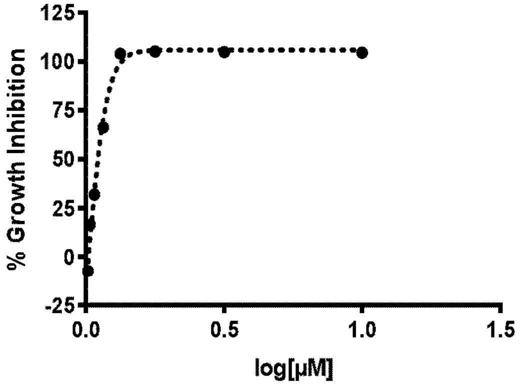
FIG. 14 presents the activity curve for a 3-nitro-2-phenyl-2H-chromene-based compound (compound no. 26) against *T. brucei.*
Figure 15:
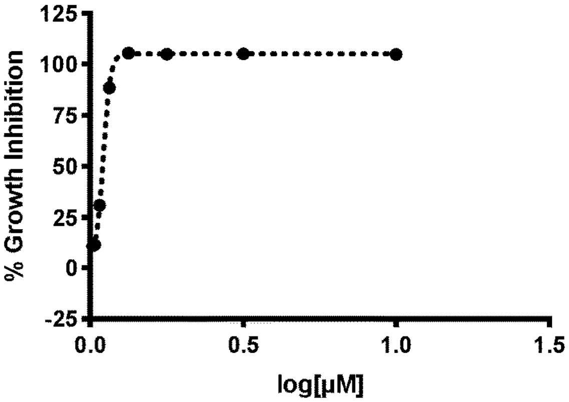
FIG. 15 presents the activity curve for a 3-nitro-2-phenyl-2H-chromene-based compound (compound no. 27) against *T. brucei.*
Figure 16:
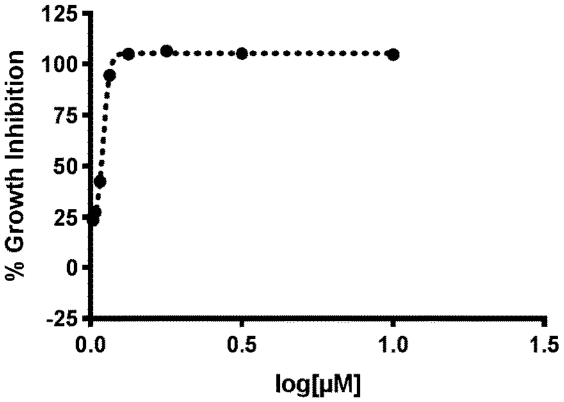
FIG. 16 presents the activity curve for a 3-nitro-2-phenyl-2H-chromene-based compound (compound no. 28) against *T. brucei.*
Figure 17:
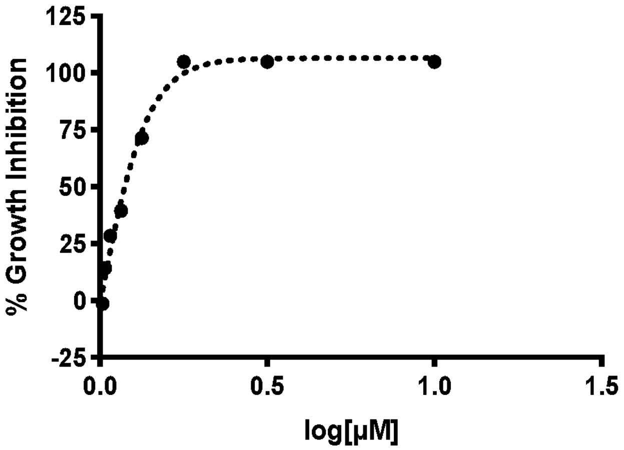
FIG. 17 presents the activity curve for a 3-nitro-2-phenyl-2H-chromene-based compound (compound no. 29) against *T. brucei.*
Figure 18:
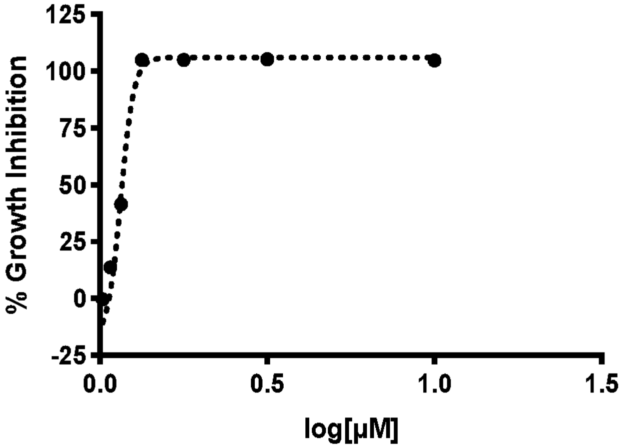
FIG. 18 presents the activity curve for a 3-nitro-2-phenyl-2H-chromene-based compound (compound no. 30) against *T. brucei.*
Figure 19:
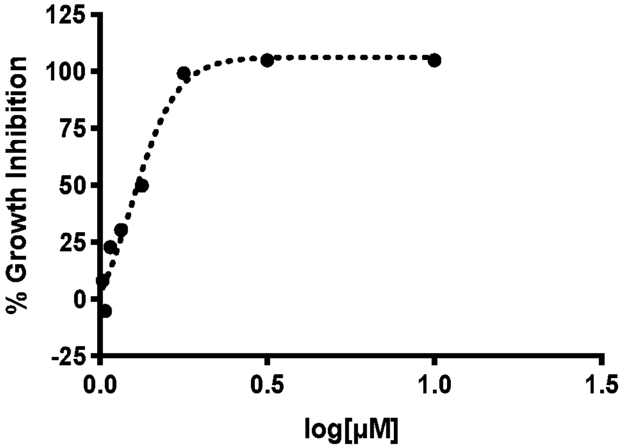
FIG. 19 presents the activity curve for a 3-nitro-2-phenyl-2H-chromene-based compound (compound no. 31) against *T. brucei.*

Compounds 1 and 5 were part of the D-GlcN series and compounds 14 and 16 were part of the D-GalN series, which indicated that compounds belonging to the D-ManN series (FIG. 1) were the least potent against a *T. cruzi* parasite infection (infective form) of mammalian cells. Plots of $IC_{50}$ for compounds 5, 14, and 16 are shown in FIG. 6 and have values of 27.24±3.74 μM for compound no. 5 (a), 19.93±3.28 μM for compound no. 14 (b), and 20.25±2.53 μM for compound no. 16 (c). Compound 1 gave rise to a previously measured $IC_{50}$ of 16.08±0.16 μM. None of the newly synthesized compounds (2-18) afforded an anti-*T. cruzi* effect that exceeded the control, compound no. 1. Since TcGlcK inhibition percentages (e.g., TcGlcK Inh20; Table 5) of the top four compounds were close to each other, a formal Ki value for compound no. 5 was selected for a comprehensive measurement. In this way, information pertaining to enzyme—inhibitor binding strength and mode of inhibition could be thoroughly understood. TcGlcK and compound no. 5 revealed a Ki of 139±35 μM (N=3) and featured competitive inhibition. Although the Ki values were not determined for compounds 14 and 16, their values were expected to be similar to that of compound no. 5. Finally, compound no. 1 was observed to have a Ki value that was stronger than compound 5 by a magnitude of 4.3-fold.

In order to determine if TcGlcK exhibited a broad substrate range, common monosaccharides were tested for TcGlcK activity. When substrate concentrations were set to 15 mM, relative to having 100% activity observed for TcGlcK and D-glucose, notable activity was observed for D-fructose (18.9%), some activity was observed for D-mannose (6.18%), and no activity was observed for D-galactose (0.00%). By increasing substrate concentrations upward to 50 mM (3.33-fold increase), TcGlcK activity also increased in a fairly similar manner, in which a 2.58-fold increase was observed for D-fructose (48.8%), a 2.69-fold increase was observed for D-mannose (16.6%), and no changes in activity were detected by using D-galactose (0.00%). All phosphorylated hexoses were shown getting converted into their corresponding products by G6PDH, in abundant quantities through a 30-second time frame. This permitted the standard TcGlcK colorimetric assay, which was timed for 110 seconds, to be used as an assay to analyze alternative substrates. Strikingly, these results confirmed TcGlcK to be a glucokinase having a broad substrate range for common hexoses.

Compound nos. 14 and 16, which are part of the D-GalN scaffold series exhibited relatively exceptional TcGlcK inhibition on the notion that D-galactose was absent of any substrate conversion. If these compounds are TcGlcK competitive inhibitors, which was not studied, this could be reasoned by subtle positioning changes in the D-glucose binding site. From structural studies, TcGlcK residues observed in D-glucose (or D-GlcN scaffold) binding included E236, E207, D131, and N130 where hydrogen bonds served as the primary intermolecular interaction stabilizing a D-glucose or D-GlcN scaffold.

Example 2

Primary assay screens of TcGlcK, LbGlcK, and HsHxKIV against the 3-nitro-2-phenyl-2H-chromene-based inhibitors compound nos. 19-22 were carried out. Compound 1, Benzoyl glucosamine (BENZ-GlcN or simply "BENZ") and carboxybenzyl glucosamine (CBZ-GlcN or simply "CBZ") were both used as controls due to their known inhibition against TcGlcK. LbGlcK was chosen to be tested against these compounds due to its 44% protein sequence similarity to TcGlcK.

All screens were done in triplicate and were analyzed using normalized percent inhibition (NPI) calculations. NPI calculations rely on positive and negative assay controls within the screen to account for any fluctuations in the fluorescence measurements. NPI provides an inhibition percentage of how each compound inhibited the given trypanosomatid glucokinase.

Results are provided in Table 7, below. The NPI for a compound to be considered a "hit" against TcGlcK required a value exceeding 60.5% inhibition in the primary screen. All four compounds (compound nos. 19-21) qualified as hits based off of this parameter. LbGlcK required compounds to be above 12.6% inhibition in its primary screen; all four compounds were also qualified as hits. The same four compounds inhibited HsHxKIV strongly, and therefore, parasite homologue selectivity was not assigned.

TABLE 7

| Compound ID | NPI (%) TcGlcK | NPI (%) LbGlcK | NPI (%) HsHxKIV |
|---|---|---|---|
| 19 | 62.3 | 25.4 | 82.1 |
| 20 | 89.5 | 21.7 | 64.7 |
| 21 | 54.7 | 15.7 | 51.8 |
| 22 | 69.5 | 23.7 | 66.0 |
| BENZ | 100 | 27.2 | 9.30 |
| CBZ-GlcN | 100 | 27.0 | 15.0 |

The results were as expected due to the similarity of the protein sequence between TcGlcK and LbGlcK. The data showed a significant amount of inhibition toward TcGlcK, and included accurate measurements for the controls, which indicates that the primary screening assay for TcGlcK was run precisely and accurately. Despite the LbGlcK primary screening assay running accurately and precise, the compounds were not as effective in inhibiting the LbGlcK enzyme in the same respect as they did for TcGlcK. HsHxKIV data show that these compounds had very high inhibition levels, which could lead to host cell apoptosis (cytotoxicity).

Example 3

Compounds 19-31 were screened against *T. brucei*. The single dose in vitro study included administration of the compounds in increasing concentrations up to 10 μM (N=3 for each compound concentration value). Media and *T. bricei*+0.5% SDS were used as control.

Table 8 shows the average $IC_{50}$ values for each compound and FIG. 7-FIG. 19 provide the % Activity determined for compound no. 19-31.

TABLE 8

| Compound no. | $IC_{50}$ (μM) |
|---|---|
| 19 | 0.902 |
| 20 | 0.862 |
| 21 | 1.67 |
| 22 | 1.28 |
| 23 | 0.614 |
| 24 | 1.19 |
| 25 | 0.515 |
| 26 | 0.435 |
| 27 | 0.416 |
| 28 | 0.356 |
| 29 | 0.743 |
| 30 | 0.664 |
| 31 | 1.12 |

These and other modifications and variations to the present invention may be practiced by those of ordinary skill in the art, without departing from the spirit and scope of the present invention, which is more particularly set forth in the appended claims. In addition, it should be understood that the aspects of the various embodiments may be interchanged both in whole or in part. Furthermore, those of ordinary skill in the art will appreciate that the foregoing description is by way of example only and is not intended to limit the invention so further described in the appended claims.

What is claimed:

1. A method of treating a kinetoplastid infection in a subject that is infected by a kinetoplastid parasite, the method comprising administering to the subject a pharmaceutical composition comprising a glucosamine derivative having the following structure:

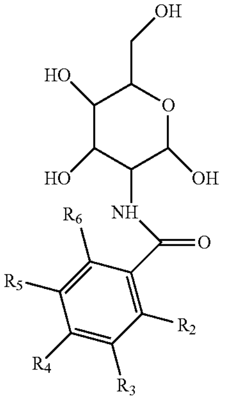

in which $R_2$, $R_3$, $R_4$, $R_5$ and $R_6$ are independently selected from hydrogen, halogen (F, Cl, Br, I) and C1-C6 alkyl halogen and at least one of $R_2$, $R_3$, $R_4$, $R_5$, and $R_6$ is a halogen or a C1-C6 alkyl halogen.

2. The method of claim 1, wherein the glucosamine derivative is a galactosamine derivative, a mannosamine derivative, or a fructosamine derivative.

3. The method of claim 1, wherein the glucosamine derivative has one of the following structures:

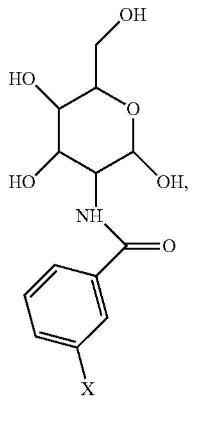

or

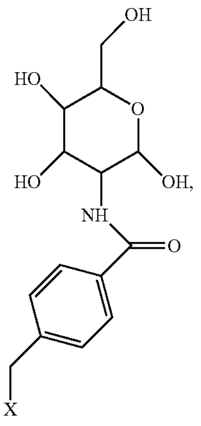

in which X is F, Cl, Br, or I.

4. The method of claim 3, wherein the glucosamine derivative has one of the following structures:

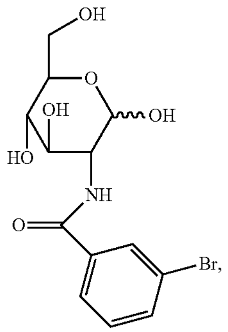

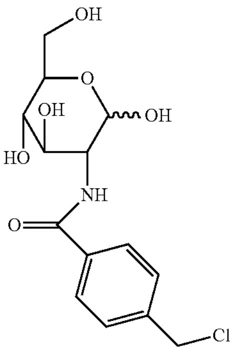

.

5. The method of claim 3, wherein the glucosamine derivative has one of the following structures:

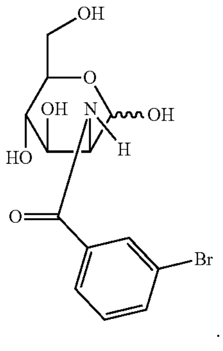

. or

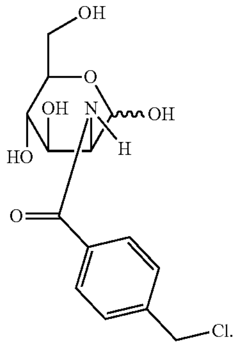

6. A method of treating a kinetoplastid infection in a subject that is infected by a kinetoplastid parasite, the method comprising administering to the subject a pharmaceutical composition comprising a glucosamine derivative having the following structure:

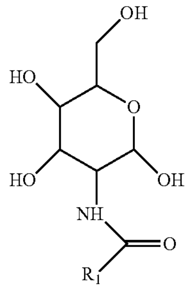

wherein $R_1$ comprises a furan, an alkylfuran, or a benzofuran in which the furan-based group makes connection via the C2 or the C3 of the furan group.

7. The method of claim 6, wherein the glucosamine derivative has one of the following structures:

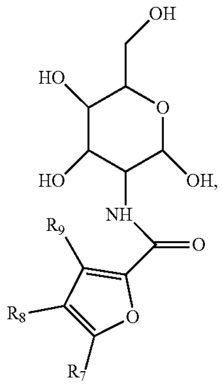

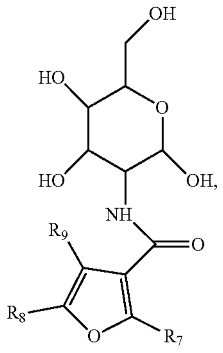

or

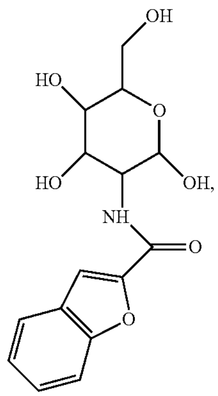

wherein $R_7$, $R_8$, and $R_9$ are independently selected from hydrogen, C1-C6 alkyl, halogen, or C1-C6 alkyl halogen.

8. The method of claim 7, wherein the glucosamine derivative has the following structure:

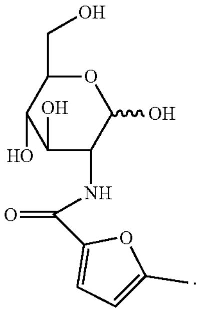

9. The method of claim 7, wherein the glucosamine derivative has one of the following structures:

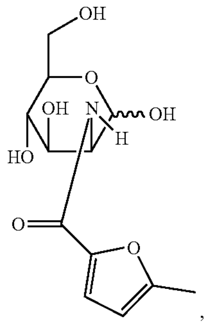

,

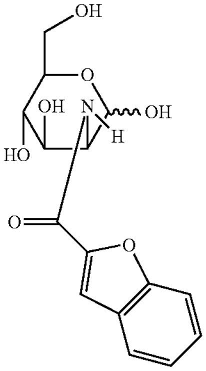

, and

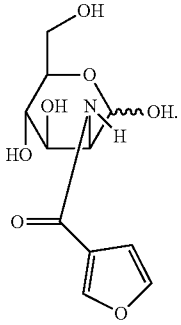

10. A pharmaceutical composition comprising a 3-nitro-2-phenyl-2H-chromene compound having the following structure:

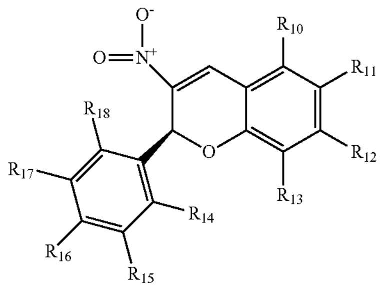

in which $R_{10}$, $R_{11}$, $R_{12}$, $R_{13}$, $R_{14}$, $R_{15}$, $R_{16}$, $R_{17}$, and $R_{18}$ are independently selected from hydrogen, halogen, C1-C4 alkyl halogen, C1-C4 alkyl, C1-C4 alkoxy, or any two adjacent of which are components of a ring fused to the respective aryl group including conjugated and non-conjugated rings, including heterocyclic rings and derivatized rings derivatized with one or more of hydrogen, halogen, C1-C4 alkyl halogen, C1-C4 alkyl, C1-C4 alkoxy, and in which at least one of $R_{14}$ and $R_{18}$ comprises a halogen.

11. The pharmaceutical composition of claim 10, in which $R_{10}$, $R_{11}$, $R_{12}$, $R_{13}$, are independently selected from hydrogen, halogen, or any two adjacent of which are components of a conjugated ring fused to the aryl group, and $R_{15}$, $R_{16}$, $R_{17}$ are independently selected from hydrogen, C1-C4 alkoxy, or any two adjacent of which are components of a conjugated or non-conjugated ring fused to the aryl group in which the ring can optionally be a heterocyclic ring.

12. A method of treating a kinetoplastid infection in a subject that is infected by a kinetoplastid parasite, the method comprising administering to the subject the pharmaceutical composition of claim 10.

13. A pharmaceutical composition comprising a 3 nitro-2-phenyl-2H-chromene compound selected from the group consisting of 2 (2,6-Dichlorophenyl)-6,8-dibromo-3-nitro-2H-chromene, 6-Bromo-2-(2-chlorophenyl)-3-nitro-2H-chromene, 2-(2-Chlorophenyl)-3-nitro-2H-chromene, 2-(2,6-Dichlorophenyl)-3-nitro-2H-chromene, 6-Bromo-2-(4-ethoxy-3-methoxyphenyl)-3-nitro-2H-chromene, 6-Bromo-2-(3,4-diethoxyphenyl)-3-nitro-2H-chromene, 6-Bromo-2-(3,4-dimethoxyphenyl)-8-methoxy-3-nitro-2H-chromene, 6-Bromo-2-(3,4-dimethoxyphenyl)-3-nitro-2H-chromene, 6,8-Dibromo-2-(3,4-dimethoxyphenyl)-3-nitro-2H-chromene, 6,8-Dibromo-2-(4-ethoxy-3-methoxyphenyl)-3-nitro-2H-chromene, 6-Bromo-2-(4-ethoxy-3-methoxyphenyl)-8-methoxy-3-nitro-2H-chromene, 6,8-Dichloro-2-(3,4-diethoxyphenyl)-3-nitro-2H-chromene, and 2-(3,4-Diethoxyphenyl)-3-nitro-2H-chromene.

14. A method of treating a kinetoplastid infection in a subject that is infected by a kinetoplastid parasite, the method comprising administering to the subject the pharmaceutical composition of claim 13.

* * * * *